United States Patent [19]

Kluttz et al.

[11] 4,395,372
[45] Jul. 26, 1983

[54] ALKYLATION PROCESS

[75] Inventors: Robert Q. Kluttz, Houston; Lynn H. Slaugh, Cypress, both of Tex.

[73] Assignee: Shell Oil Company, Houston, Tex.

[21] Appl. No.: 406,665

[22] Filed: Aug. 9, 1982

[51] Int. Cl.³ .................. C07C 121/52; C07B 27/00; C07C 2/66
[52] U.S. Cl. .............................. 260/465 R; 568/628; 568/939; 570/257; 585/467
[58] Field of Search ................... 260/465 R; 585/467; 568/628, 939; 570/257

[56] References Cited

U.S. PATENT DOCUMENTS 2,882,244  4/1959  Milton ................................. 252/455
3,216,789  11/1965  Breck et al. ........................ 23/113
4,302,622  11/1981  Chu ..................................... 585/467

OTHER PUBLICATIONS

Flockhart et al., Journal of Catalysis, vol. 72, 314–321 (1981).

Primary Examiner—Dolph H. Torrence

[57] ABSTRACT

A process is disclosed for alkylation of benzenes with lower olefins which comprises contacting the benzene and lower olefin with a rare earth exchanged X or Y zeolite catalyst in the presence of sulfur dioxide.

6 Claims, No Drawings

ALKYLATION PROCESS

FIELD OF THE INVENTION

This invention relates to a process for alkylating benzene and substituted benzenes with lower olefins.

BACKGROUND OF THE INVENTION

Flockhart et al (J. of Catalysis), 72, 314–321 (1981)) discloses the use of rare-earth-exchanged forms of X and Y qualities for the catalytic alkylation of benzene and substituted benzenes.

SUMMARY OF THE INVENTION

The instant invention relates to a process for alkylating benzene and substituted benzenes with lower olefins, which process comprises contacting the benzene or substituted benzene and the olefin with a rare-earth-exchanged faujasite-type zeolite in the presence of sulfur dioxide. The use of sulfur dioxide in the reaction mixture enhances selectivity to the mono-alkylated product over that selectivity produced in the absence of sulfur dioxide.

DESCRIPTION OF THE PREFERRED EMBODIMENTS

The instant process comprises alkylating benzene or substituted benzenes with lower olefins utilizing a catalyst system comprising a rare-earth-exchanged faujasite-type zeolite and sulfur dioxide. The presence of sulfur dioxide in the reaction mixture in some fashion modifies the zeolite catalyst to produce an enhanced conversion to the mono-alkylated product. As used herein, the term "mono-alkylated product" refers to a product prepared from a given benzenoid compound by adding one alkyl group to the benzene ring. The mono-alkylated product would thus have one more alkyl group than the starting material. For example, when the starting material was a xylene, the mono-alkylated product would be a trialkylbenzene.

The feed materials to be alkylated comprise benzene and substituted benzenes. Substituted benzenes comprise those having substituent groups inert to the alkylation reaction conditions. Typical substituents include alkyl, halo, alkoxy, cyano, nitro and the like. Preferred substituted benzene materials are the alkyl-substituted benzenes, preferably the lower alkyl-substituted benzenes wherein the alkyl-substituents have carbon numbers ranging from 1 to about 6.

The alkylating olefins comprise olefins having carbon numbers ranging from 3 to about 6. Suitable olefins are propylene, butylenes, pentenes and hexenes. Ethylene has been found not to be satisfactory for use with the instant catalytic system.

The zeolites used in the catalytic system in the instant invention are of the faujasite type and are at least partially exchanged with the rare-earths, that is, a portion of the various exchange sites are satisfied by rare-earth ions. Preferably at least 50% of the exchange sites are satisfied by rare-earth ions. Typical faujasite zeolites are described in U.S. Pat. Nos. 2,882,244, usually referred to as X zeolites and 3,216,789, usually referred to as Y zeolites. X and Y zeolites are preferred species. The faujasitic-type zeolites have been widely employed in catalytic processes such as for the conversion of hydrocarbons and are generally well known. The patent and general literature is extensive on these. In a typical preparation of a rare-earth exchanged zeolite, the sodium form of the faujasite type zeolite is contacted with a solution of a rare-earth salt whereby the rare-earth ion is ion exchanged, at least in part, with the sodium ion. The term "rare-earth" as used herein refers to those elements in the Periodic Table with atomic numbers ranging from 57 to 71. Any suitable, soluble rare-earth salt can be utilized, dissolved in an appropriate solvent, for ion exchanging with the sodium in the zeolite. Suitable salts and solvents are readily determined by one skilled in the art. Illustrative examples of rare-earth salts would be rare-earth chlorides, bromides, iodides, nitrates, sulfates, oxalates, acetates, proprionates, acetylacetonates, fluoroacetates, octanoates, naphthanates, valerates and the like.

The zeolitic catalytic material is used in a fashion typical of that utilized for heterogeneous catalysts. It may be used in fixed beds, in fluidized beds or in batch reactors.

The addition of the sulfur dioxide, which is a critical aspect of this invention, is carried out in an appropriate fashion. In a continuous reaction process, the sulfur dioxide is typically added to the feed or injected into the reactor simultaneously with the feed and then the reactor is heated to reaction conditions. In a batch reactor the charging of the reactor with sulfur dioxide may be concurrent or separate from the charging of the feed and either feed or sulfur dioxide may be charged before or after reaction conditions are reached. Suitable concentrations of sulfur dioxide in the reaction mixture range for about 0.005 to about 1.0 moles per liter. Higher concentrations of sulfur dioxide are needed at higher temperatures. This is believed due to a temperature sensitive equilibrium between the sulfur dioxide and the zeolite which requires a higher concentration of sulfur dioxide at higher temperatures to achieve the same effect.

The instant invention thus comprises an improved process for alkylating benzene and substituted benzenes with olefins and enhanced selectivity to mono-alkylated product by contacting said benzene or substituted benzene and said olefin with a rare-earth-exchanged zeolite, wherein the improvement comprises carrying out the reaction in the presence of sulfur dioxide.

The process of the instant invention will be further described below by the following illustrative embodiments which are provided for illustration and are not to be construed as limiting the invention.

ILLUSTRATIVE EMBODIMENTS

The following example illustrates the typical preparation at a rare-earth-exchanged zeolite useful in the process of the instant invention.

One hundred grams of X-type zeolite (Linde 13X) were slurried in one liter of water containing 100 g of cerium trichloride for 24 hours at room temperature. The slurry was filtered and repeatedly washed until the filtrate contained no chloride ion. This procedure was repeated and the catalyst was then oven dried at 100° C. Exchange levels were approximately 60%. The zeolites were calcined in air at 5° C./min. heating rate to 500° C. which was maintained overnight.

The following illustrates a process according to the instant invention.

Cerium-exchanged zeolite catalysts were prepared as described above using a Y-type zeolite (Union Carbide, SK-40) and an X-type zeolite (Linde 13X). Then, to a 300 cc Hastelloy B autoclave was charged 100 g of dry benzene, 5 g of decane (as an internal standard for analytical workup), and 0.5 g of cerium-exchanged zeolite under a nitrogen atmosphere. The desired amount of sulfur dioxide was weighed into a Hoch vessel and was pressured into the autoclave with nitrogen. (A control experiment without sulfur dioxide was also run.) The autoclave was heated to reaction temperatures and 5.0 g of propylene was introduced under nitrogen pressure (total 800 psi). The liquid phase was monitored by GC using a 10′ column packed with 5% SE-30 on Chromasorb 101. The results are shown in Tables 1 and 2.

TABLE 1

Alkylation of Benzene with Propylene[a] Using Cerium-Exchanged Linde 13X Zeolite and $SO_2$

| Sulfur Dioxide | 0 | 0.05 g | 0.5 g | 1 g | 3 g | 5 g | 10 g |
|---|---|---|---|---|---|---|---|
| | | | 120° C. | | | | |
| Conversion of $C_3^=$ | 53% | 52% | 47% | 79% | 93% | 96% | 49% |
| Selectivity[b] | 89.7% | 93.6% | 94.5% | 95.7% | 95.5% | 95.8% | 97.0% |
| m/p[c] | 0.851 | 0.598 | — | 0.671 | 0.616 | 0.545 | 0.551 |
| | | | 140° C. | | | | |
| Conversion of $C_3^=$ | 73% | 78% | 74% | 79% | 99% | 95% | 36% |
| Selectivity | 90.2% | 88.4% | 90.5% | 93.1% | 93.9% | 94.5% | 94.9% |
| m/p | 0.858 | 0.880 | 0.871 | 0.659 | 0.643 | 0.605 | 0.651 |

[a]100 g benzene, 5 g propylene, 0.5 g catalyst; 90 minute samples
[b]Selectivity for mono vs. dialkylated product
[c]Meta/para diisopropylbenzene.

TABLE 2

Alkylation of Benzene with Propylene[a] Using Cerium-Exchanged SK-40 Zeolite and $SO_2$

| Sulfur Dioxide | 0 | 0.05 g | 0.5 g | 10 g |
|---|---|---|---|---|
| | | 120° C. | | |
| Conversion of $C_3^=$ | 32% | 44% | 49% | — |
| Selectivity[b] | 93.4% | 93.7% | 93.7% | 94.3% |
| m/p[c] | .791 | .734 | .746 | .756 |
| | | 140° C. | | |
| Conversion of $C_3^=$ | 74% | 70% | — | 75% |
| Selectivity | 87.3% | 88.5% | 88.9% | 91.8% |
| m/p | 1.05 | 1.03 | 1.07 | .77 |

[a]100 g benzene, 5 g propylene, 0.5 g catalyst; 90 minute samples
[b]Selectivity for mono vs. dialkylated product
[c]Meta/para diisopropylbenzene.

When toluene was reacted with propylene at 130° C. using a cerium-exchanged Linde 13X zeolite catalyst, mono-alkylated product was produced with a selectivity of 89.3% when 3 g of $SO_2$ was added to the reaction, the selectivity increased to 93.8%.

When benzene was reacted with 1-butene at 130° C. using a cerium-exchanged Linde 13X zeolite catalyst, 2-phenyl butane was obtained with 97.3% selectivity without $SO_2$. Upon addition of $SO_2$, the selectivity increased to greater than 99%.

We claim:

1. A process for alkylating benzene and substituted benzenes with olefins having carbon numbers ranging from 3 to about 6 which process comprises contacting said benzene or substituted benzene with said olefin at a temperature ranging from about 50° C. to about 300° C. and a pressure ranging from about 1 to about 200 atmospheres with a rare-earth-exchanged zeolite in the presence of sulfur dioxide.

2. The process of claim 1 wherein the zeolite is a faujasite type.

3. The process of claim 2 wherein zeolite is an X-zeolite or a Y-zeolite.

4. The process of claim 1 wherein the zeolite is at least fifty percent exchanged with the rare earth.

5. The process of claim 4 wherein the rare earth is lanthanum or cerium.

6. The process of claim 1 wherein the sulfur dioxide concentration in the reaction mixture ranges from about 0.005 to about 1.0 moles per liter.

* * * * *